United States Patent
Graves et al.

(10) Patent No.: US 9,274,042 B2
(45) Date of Patent: Mar. 1, 2016

(54) SPATIALLY CORRELATED LIGHT COLLECTION FROM MULTIPLE SAMPLE STREAMS EXCITED WITH A LINE FOCUSED LIGHT SOURCE

(71) Applicants: Steven Wayde Graves, Santa Fe, NM (US); Pearlson Prashanth Austin Suthanthiraraj, Albuquerque, NM (US); Andrew P. Shreve, Santa Fe, NM (US); Gabriel P Lopez, Durham, NC (US)

(72) Inventors: Steven Wayde Graves, Santa Fe, NM (US); Pearlson Prashanth Austin Suthanthiraraj, Albuquerque, NM (US); Andrew P. Shreve, Santa Fe, NM (US); Gabriel P Lopez, Durham, NC (US)

(73) Assignee: STC.UNM, Albuquerque, NM (US)

( * ) Notice: Subject to any disclaimer, the term of this patent is extended or adjusted under 35 U.S.C. 154(b) by 78 days.

(21) Appl. No.: 13/835,108

(22) Filed: Mar. 15, 2013

(65) Prior Publication Data

US 2013/0214176 A1    Aug. 22, 2013

Related U.S. Application Data

(63) Continuation-in-part of application No. 13/103,756, filed on May 9, 2011, now Pat. No. 8,830,451.

(60) Provisional application No. 61/662,541, filed on Jun. 21, 2012, provisional application No. 61/395,190, filed on May 7, 2010.

(51) Int. Cl.
*G01N 21/00* (2006.01)
*G01N 15/14* (2006.01)
*G01N 21/64* (2006.01)

(52) U.S. Cl.
CPC ............ *G01N 15/14* (2013.01); *G01N 15/1404* (2013.01); *G01N 15/1434* (2013.01); *G01N 15/1484* (2013.01); *G01N 21/64* (2013.01); *G01N 15/1459* (2013.01); *G01N 2015/142* (2013.01)

(58) Field of Classification Search
CPC .......... G01N 15/1459; G01N 15/1434; G01N 15/0205; G01N 1/4077
USPC .................................. 356/335, 338, 244, 246
See application file for complete search history.

(56) References Cited

U.S. PATENT DOCUMENTS 3,705,771 A * 12/1972 Friedman et al. ............... 356/39
5,313,264 A * 5/1994 Ivarsson et al. ................ 356/73

(Continued)

FOREIGN PATENT DOCUMENTS

KR    1020090034245    4/2009
WO    2011017681 A2    2/2011

OTHER PUBLICATIONS

W. G. Eisert, "High Resolution Optics Combined with High Spatial Reproducibility in Flow", Aug. 25, 1980.*

(Continued)

*Primary Examiner* — Gregory J Toatley
*Assistant Examiner* — Maurice Smith
(74) *Attorney, Agent, or Firm* — Gonzales Patent Services; Ellen M. Gonzales (57) ABSTRACT

An affordable flow cytometry system with a significantly increased analytical rate, volumetric sample delivery and usable particle size including a light beam that interrogates multiple flow streams so as to provide excitation across all of the streams, and an optical objective configured to collect light from the sample streams and image the light onto an array detector.

25 Claims, 4 Drawing Sheets

(56) References Cited

U.S. PATENT DOCUMENTS

| | | | |
|---|---|---|---|
| 6,454,945 B1* | 9/2002 | Weigl et al. | 210/634 |
| 7,217,393 B2 | 5/2007 | Witty et al. | |
| 7,576,861 B2* | 8/2009 | Gilbert et al. | 356/436 |
| 7,709,821 B2 | 5/2010 | Casstevens et al. | |
| 2004/0184960 A1 | 9/2004 | Tanaami | |
| 2006/0037915 A1* | 2/2006 | Strand et al. | 210/748 |
| 2006/0146327 A1* | 7/2006 | Wang | G01N 15/0266 356/338 |
| 2008/0176216 A1* | 7/2008 | Doyle et al. | 435/5 |
| 2008/0245745 A1* | 10/2008 | Ward et al. | 210/748 |
| 2009/0244536 A1* | 10/2009 | Mitchell et al. | 356/343 |

OTHER PUBLICATIONS

Surendara Ravula. "A microfluidic system combining acoustic and dielectrophoretic particle preconcentration and focusing", Oct. 3, 2007.*

G. Eisert, "High Resolution Optics Combined with High Spatial Reproducibility in Flow", Aug. 25, 1980.*

\* cited by examiner

FIG. 11

SPATIALLY CORRELATED LIGHT COLLECTION FROM MULTIPLE SAMPLE STREAMS EXCITED WITH A LINE FOCUSED LIGHT SOURCE

CROSS-REFERENCE TO RELATED APPLICATIONS

The following application claims the benefit of U.S. Provisional Application No. 61/662,541, filed Jun. 21, 2012, which is hereby incorporated by reference in its entirety. The following application is also a continuation in part of U.S. application Ser. No. 13/103,756, filed May 5, 2011, which claims the benefit of U.S. Provisional Application 61/395,190, filed May 7, 2010.

STATEMENT REGARDING GOVERNMENT SPONSORED RESEARCH

This invention was made with Government support under Grant No. RR020064 awarded by The National Institutes of Health (NIH). The U.S. Government has certain rights in this invention.

BACKGROUND

The analytical power of flow cytometry makes it invaluable for numerous biomedical applications that require the enumeration of cell populations and the analysis of multicellular model systems or organisms. However, typical flow cytometers limit sample analysis flow to less than 250 µL/min, analytical rates to 70,000 cells/s, and particle diameters to less than 70 µm. These limitations are driven by a number of factors that include pressure induced by high linear velocity fluid flows, turbulence in wide channels, and the single point analysis of stochastically arriving particles. Therefore, flow cytometry requires significant additional sample preparation steps to be effective in the analysis of very rare cell populations, uses offline particle concentration to analyze particles in large volume samples, and requires special purpose large flow channel cytometers using low linear velocity hydrodynamic focusing in wide channels to analyze particles that are >70 µm in diameter at low analysis rates (200 particle/s). Such limitations severely reduce the effectiveness of flow cytometry in many critical applications including the detection of rare blood cell populations, the detection of pathogens in liquid samples, and large particle high throughput analysis model systems (e.g. multicellular model organisms, cellular spheroids, and one-bead-one-compound chemical libraries).

Therefore there is a great need for affordable flow cytometry systems that have an increased analytical rate, volumetric sample delivery and usable particle size while retaining the analytical properties of flow cytometry (sensitivity, resolution of free vs. bound probes, correlated multiparameter analysis) that make it the technology of choice for cell and particle analysis.

SUMMARY

The present disclosure provides an affordable flow cytometry system with a significantly increased analytical rate, volumetric sample delivery and usable particle size compared to previously described flow cytometry systems. According to various embodiments the present disclosure provides a system for detecting particles in multiple flow streams. The system may include a light beam that interrogates multiple flow streams and provides excitation across all of the streams, and an optical objective configured to collect light from the sample streams and image the light onto an array detector. In general, the light emitted from each flow stream can be individually identified and distinguished from light emitted from any other flow stream by its location on the array detector. According to some embodiments the multiple flow streams are achieved through the use of acoustic waves.

DETAILED DESCRIPTION

According to an embodiment the present disclosure provides an affordable flow cytometry system with a significantly increased analytical rate, volumetric sample delivery and usable particle size compared to previously described flow cytometry systems. In general, the system described herein is able to analyze cells or particles ranging from 1 to 1000 µm in diameter, at flow rates of up to 50 mL/min, and at rates of up to $1 \times 10^6$ particles/second. According to a specific embodiment, the presently described system is able to generate up to 300 focused parallel streams of particles using both acoustically resonant microfabricated channels and multi-node acoustic standing waves. These flow cells focus particles up to 200 µm in diameter at volumetric delivery rates as high as 25 mL/min.

It will be understood that while much of the description herein is directed towards flow cytometry applications, many of the mechanisms described herein are applicable to any system where it is desirable to measure or detect particle flow through time. Examples of other suitable systems include HPLC and capillary electrophoresis. Likewise, it should be understood that while the present system is configured to detect particles in a flow stream, that flow stream need not necessarily be in a liquid, but could be through a gel matrix or some other equivalent.

In general, light from a laser or other suitable source is shaped, directed, and or focused into a line that extends across an entire array of individually interrogable sample streams so as to provide either even (homogenous) or uneven (inhomogenous) excitation, as desired, across the streams. Light emitted from particles excited by the light while traveling in the sample streams is then collected and imaged onto one or more array detectors. The image of the particles being interrogated by the line of light maps onto individual or small numbers of elements in the array detector. This enables elements of the array detector to be correlated with which specific sample stream they are recording. This further enables the collection of particle by particle optical properties, while recording which sample stream a particle was located in. Furthermore, the continuous collection of signal from elements in the array detector that correlate to spaces between sample streams will offer opportunities to monitor background signal for use in signal processing algorithms.

It will be understood that in contrast to previous multi stream capillary electrophoresis systems that sequentially interrogate the array of sample streams by rapidly moving a beam of light across the individual streams, resulting in particles being detected only if they happen to be travelling through the interrogation zone when the zone is being interrogated, the presently described system interrogates all sample streams simultaneously, producing a clear record of all detectable particles in every stream at all times and also reports in which stream a particle appeared. This ability enables high sensitivity and increased capabilities such as event-based detection.

Moreover, as described in greater detail below, the presently described system can be designed to include sample streams that can easily accommodate larger particles and increased flow rates. The combination of simultaneous interrogation and increased sample stream capacity results in a powerful tool for the field of particle analysis.

Figure 1:
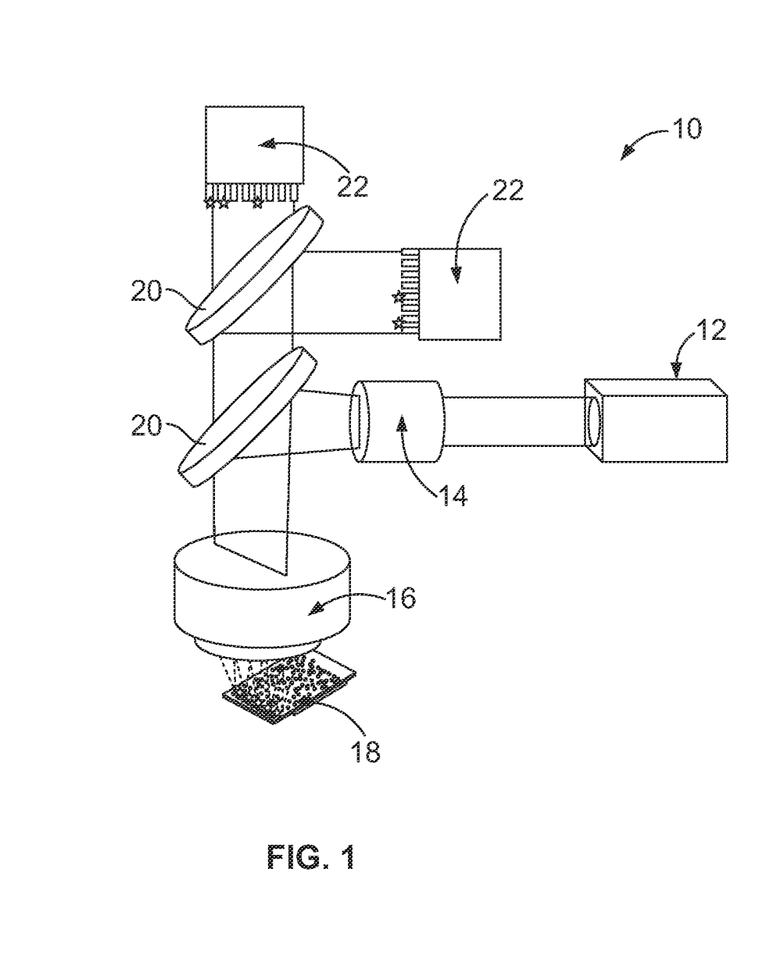
FIG. 1 is a schematic illustration of an exemplary system according to an embodiment of the present disclosure.

Turning now to FIG. 1, a first embodiment of a system 10 is shown. As depicted, system 10 includes a laser 12, beam shaper 14, an optical objective 16, a sample stream 18, beamsplitters 20 and one or more array detectors 22. As shown, laser 12 is configured to produce a standard circular or elliptically-shaped laser beam. Light from laser 12 is then directed through beam shaper 14, which may take the form, for example, of a Powell lens (commercially available, for example, from Laser Line Optics Canada, Inc, Ontario, CA), which shapes the light into a line. The line of light is then directed, via a dichroic beamsplitter towards an optical objective 16 which focuses the line of light across the entire width of the sample stream array 18, so as to simultaneously interrogate each sample stream. In the embodiment shown in FIG. 1, optical objective 16 also collects light from the sample and images the collected light onto array detector(s) 22. As shown, the collected light may be directed through one or more beamsplitters 20 before reaching the array detector(s).

Laser 12 may be a laser of any type. Alternatively, a laser diode bar may be used. Additionally, any intense light source such as a light emitting diode or an arc lamp may also be used.

The array detector(s) 22 may be any array of detectors, including multianode PMTs, emCCDs, CMOS, CCD, or other such optical detectors.

In viewing the figures, it will be seen that various minors and other optical devices may be used for bending or altering the direction of the various light beams described herein so as to enable various configurations and relative positions for the various components. However, the specific relative positions and locations of the various elements described herein or shown in the figures should in no way be considered as limiting the disclosure to the particular locations and relative positions shown or described. Moreover, those of skill in the art will be familiar with a wide variety of devices that can be used to bend or alter the direction of light beams. Accordingly, while not necessarily described in substantial detail, the use of such mechanisms and/or such various configurations is contemplated by the present disclosure. For example, the various components and devices described herein may be arranged so as to minimize the amount of space used or to fit into a specific location or area and it will be understood that a near infinite number of configurations and relative positions are possible.

According to some embodiments, optical objective 16 may take the form of an infinity corrected 10× objective having an NA 0.45. Objectives fitting these specifications are comparable to that used in commercial cytometers and have been effectively shown to support creation of a 10 µm wide, 1.6 mm long laser line. See e.g., Sinclair et al (2004) Design, construction, characterization, and application of a hyperspectral microarray scanner. *Applied Optics* 42, 2079-2088. For geometrically longer laser lines and wider fields of view, aspheric lenses such as the AL7560-A from ThorLabs, Inc (Newton, N.J., USA), having 75 mm diameter, 0.62 NA and a focal length of 60 mm might be used. The infinity corrected light path, large diameter, and high NA of this objective make it possible to produce laser lines tens of mm in length when paired with the appropriate Powell lenses. Furthermore, its high NA ensures sensitive optical collection over a wide field of view. Though these lenses give workable examples, any objective may be used here, including single element lenses (such as aspheric lenses), multi element lenses, and objectives with varying specifications.

Figure 2:
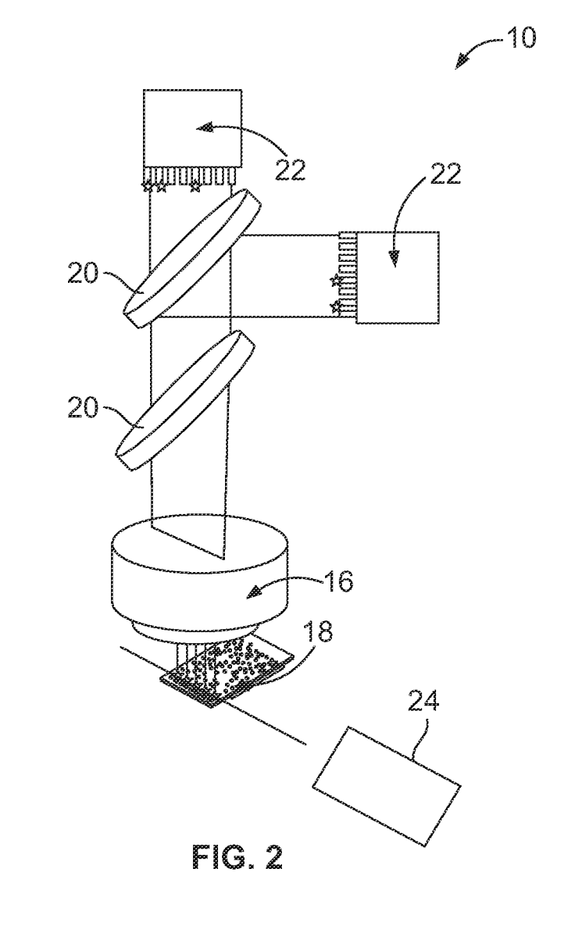
FIG. 2 is a schematic illustration of an exemplary system according to another embodiment of the present disclosure.

A second embodiment is shown in FIG. 2. In this embodiment, simultaneous interrogation of the streams of sample stream 16 is achieved by the use of a Bessel beam 24. Bessel beams are non-diffracting and self-healing laser beams that are made by focusing light through a conical lens known as an axicon. When Bessel beams are scattered off obstacles in the optical path, the scattered and unscattered light interferes to recreate the original wavefront. Accordingly, Bessel beam 24 is positioned so as to interrogate the sample stream orthogonally across the width of the flow channel, such that the self-healing properties of the beam ensure that intervening particles minimally affect the excitation of adjoining streams.

Figure 3:
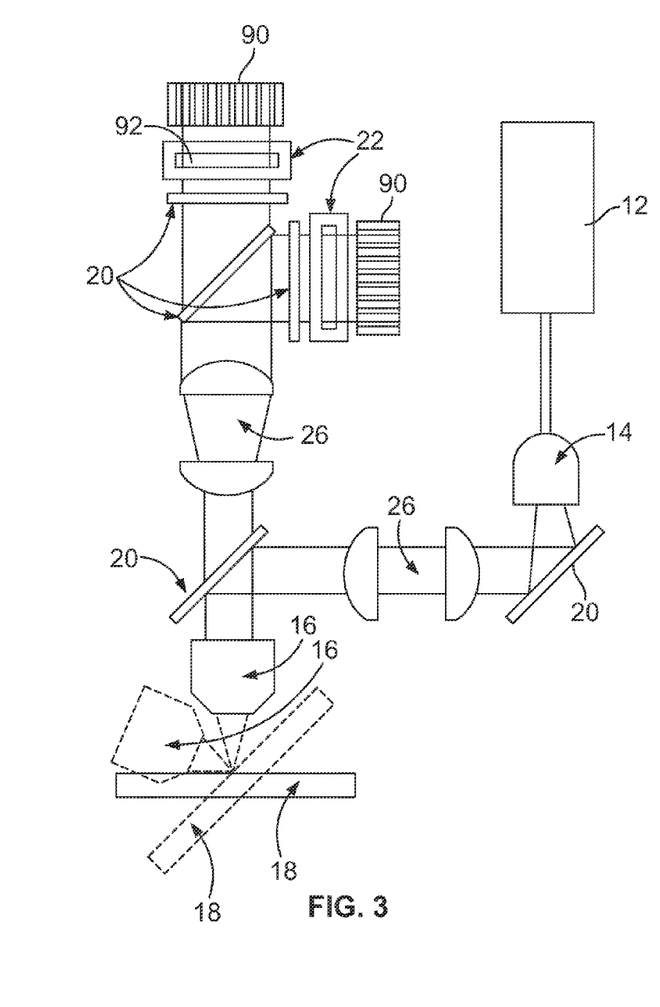
FIG. 3 is a schematic illustration of an exemplary system according to a further embodiment of the present disclosure.

A third embodiment is shown in FIG. 3. In this embodiment, telescopes 26 are used to adjust the size of the incoming or outgoing light path. As described in greater detail below, masks 90 may be placed in the image plane or slits 92 made in the focal plane of the array detectors 22 and the configuration/angle of optical objective 16 and sample stream array 18 can be altered according to various design requirements or desires.

As stated above, the system described herein includes a sample stream array. According to some embodiments, the array is able to separate a sample into a large number, even hundreds, of streams. These streams could be created by numerous approaches including: 1. the use of microfluidic channels that employ hydrodynamic focusing to position particles. 2. Dielectrophoretic focusing that uses dielectrophoresis to position particles. 3. Acoustic focusing that uses standing ultrasonic waves or surface acoustic waves to position particles. 4. Microfluidic channels that use "inertial focusing" or induced flow from microfabricated structures to position particles. Any of these methods could be used to generate a regular array of particle steams flowing past the excitation line.

Figure 4:
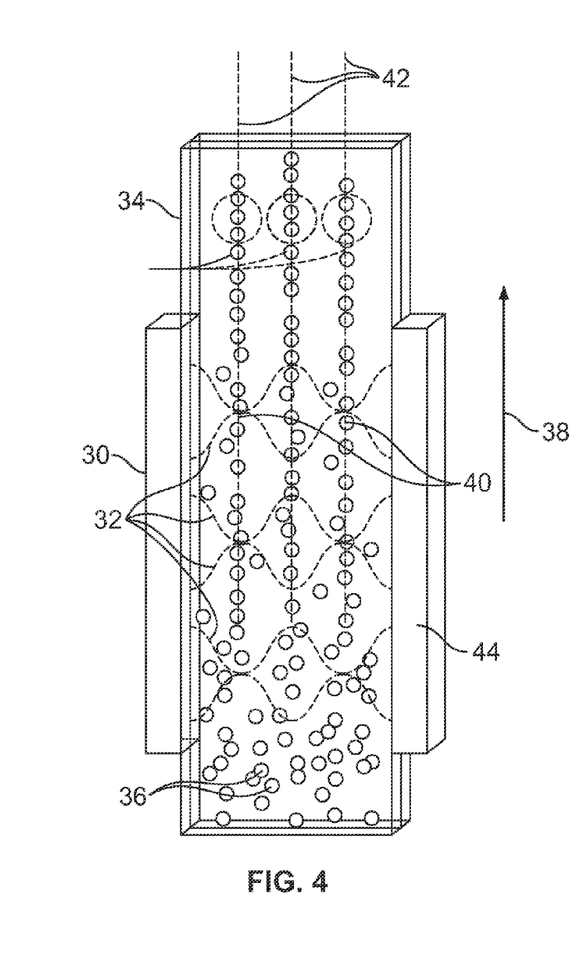
FIG. 4 is a schematic illustration of the use of acoustic focusing to produce multiple sample streams.

One mechanism for achieving an array of streams is through the use of acoustic focusing, which uses acoustic standing waves to generate multiple sample streams. The use of acoustic focusing to produce multiple sample streams suitable for use in flow cytometry and other applications is described for example, in co-pending U.S. patent application Ser. No. 13/103,756 filed Jul. 29, 2011. Briefly, as shown in FIG. 4, an acoustic wave generator 30 produces an acoustic wave field 32 across the width of a capillary or flow cell 34. Particles 36 in a sample flowing through the capillary (direction of flow shown by arrow 38) to the various nodes 40 of the wave field, produce multiple parallel particle streams 42 in the same capillary. The acoustic wave field may be produced, for example, by a piezoelectric element. In some embodiments a second piezoelectric element 44 may be placed on the opposing side of the first element to pick up feedback signals.

It will be appreciated that an acoustic wave field can be used to produce a large number of streams in a single channel. For example, we have been able to produce up to thirty seven acoustically separate streams in a single channel. For the purposes of the present disclosure, a "channel" shall refer to a physical structure that provides division while a "stream" or "flow stream" shall refer to a specific, distinguishable, pathway taken by particles within a moving fluid sample.

Furthermore, the system can be multiplexed by producing multiple parallel particle streams via acoustic focusing in multiple channels. Using a combination of channels and acoustically focused streams, it is possible to achieve up to hundreds of streams for interrogation.

Within each channel, the number of nodes per channel is defined by equation 1, below, where $C_m$ is the speed of sound in the media, N is the number of desired nodes, and W is the width of the channel in the direction that the one-dimensional acoustic wave of frequency v is propagating. As an example, we have been able to produce systems with 100 microfabricated channels where each channel contains three acoustically focused streams, resulting in a total of 300 individual streams.

$$v = \frac{C_m N}{2W} \quad \text{Equation 1}$$

To increase speed and efficiency even more, the sample streams described herein could be used in conjunction with a high throughput sampling system such as that described in Edwards et al., (2001) HTPS flow-cytometry: a novel platform for automated high throughput drug discovery and characterization. *Journal of biomolecular screening* 6, 83-90. This system can process a 384-well plate in less than 10 min when connected to a single flow cytometer (See e.g., Edwards et al., (2009) High-content screening: flow cytometry analysis. *Methods Mol Biol* 486, 151-165 and Edwards et al., Cluster cytometry for high-capacity bioanalysis. *Cytometry, Part A: the journal of the international Society for Analytical Cytology* 81, 419-429).

As a specific example, by adapting the above-described flow cells so that 1 or more flow streams are derived from a single sampling probe, and by increasing the number of sampling probes on the Edwards system to 16, we can flexibly increase sample throughput with respect to the number of samples processed and volume of each sample analyzed per unit time. For example, 16 sampling probes will enable a single system to process an entire column of a 384-well plate in a single positioning event of the sampling arm. This will decrease plate-processing time 16-fold. Alternatively, a 4-probe configuration will enable a 4-fold reduction in single cytometer plate sampling time in combination with an 4-fold increase in sample volume analyzed, which is an important feature for samples in which cells targeted for analysis represent a small fraction of total cells or in which cell concentrations are unavoidably low.

The use of an acoustic wave field also creates opportunities for the development of assays and experiments that can take advantage of the properties provided by the presence of an acoustic field. For example, positive and/or negative acoustic contrast particles can be used for sorting, isolation, and purification applications. Examples of acoustic contrast particles suitable for use with the systems described herein are disclosed in co-pending U.S. patent application Ser. No. 13/320, 476, which is a U.S. National Stage application of PCT/US10/34415, filed May 11, 2010.

Figure 5:
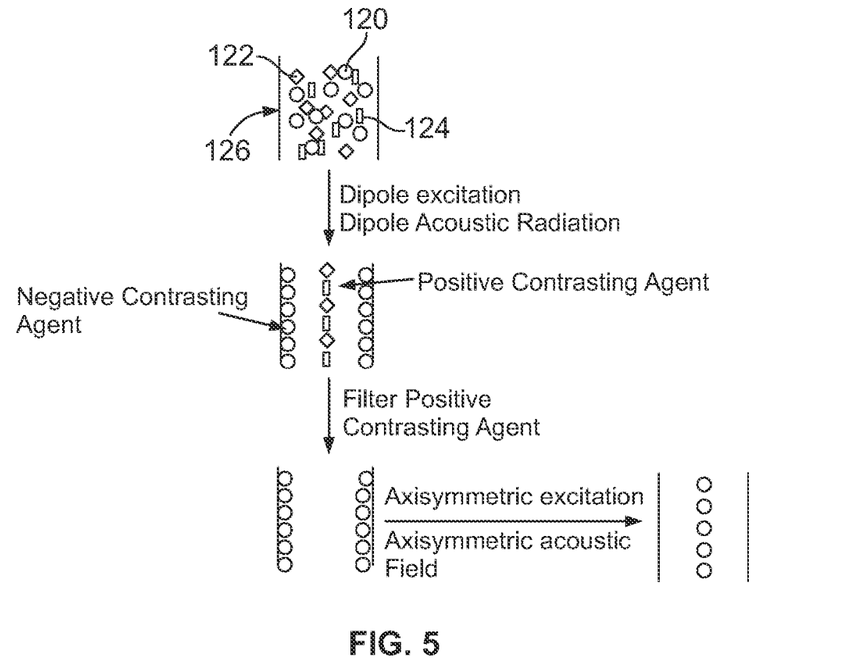
FIG. 5 is a schematic illustration demonstrating the use of negative acoustic contrast particles.

FIG. 5 is a schematic illustration demonstrating the ways in which monodisperse negative acoustic contrast particles may be used as part of a powerful bioanalytical methodology. For example, biospecific negative acoustic contrast particles 120 that have been previously mixed with a biological sample 122 can be separated from other (positive acoustic contrast) particles 124 in the sample by using acoustic pressure radiation fields (e.g. acoustic standing, cylindrical, or spherical wave fields). The acoustic pressure radiation field (e.g. acoustic dipole excitation) can focus the positive acoustic contrast particles to their pressure potential minima (e.g. pressure nodes) while focusing the negative acoustic contrast particles to their pressure potential maxima (e.g. pressure antinodes) within the flow cell. The relative position of the antinodes (containing the negative contrast particles) and the nodes (containing cells and other positive contrast particles) will map to specific locations across an array detector. Thus, using this approach for analysis will immediately allow direct measurement of the negative contrast particles, while simultaneously analyzing the positive contrast particles and cells.

Returning to FIGS. 1-3, it will be appreciated that various types of channels (with or without the addition of acoustic focusing) can be used to produce the desired number of flow streams, including hydrodynamic focusing channels used for standard flow cytometry. Examples of suitable channels include, channels formed from optically thin wall rectangular glass capillaries, channels formed by etching channels in a silicon chip, machined flow cells, and combinations thereof.

According to a specific embodiment, the system of the present disclosure includes channels formed from thick wall optically clear rectangular capillaries coupled with piezos that are designed to accommodate the specific wall dimensions. The approach has excellent optical accessibility, but in some instances, for example when the channel is used in conjunction with acoustic focusing, thick wall capillaries may not effectively transmit acoustic energy. In this case it may be desirable to use PZT drives with matched impedance to the system.

Figure 6:
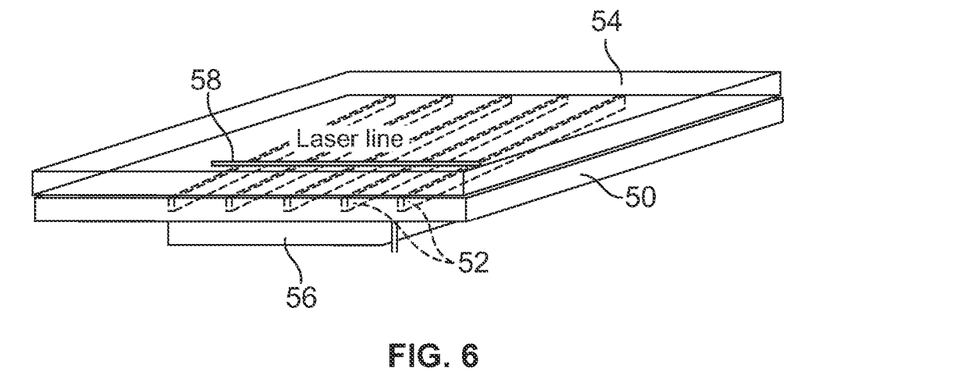
FIG. 6 is a schematic illustration of multiple sample streams according to an embodiment of the present disclosure.

FIG. 6 is a schematic illustration of another specific embodiment in which channels are etched into a glass substrate. In the depicted embodiment, the etched glass 50, including multiple channels 52, is covered with a glass top 54. As shown, an optional acoustic transducer 56 may be placed below the etched glass. This embodiment is suitable for use in a system such as that shown in FIG. 1, wherein a laser line 58, is directed onto the array.

Figure 7:
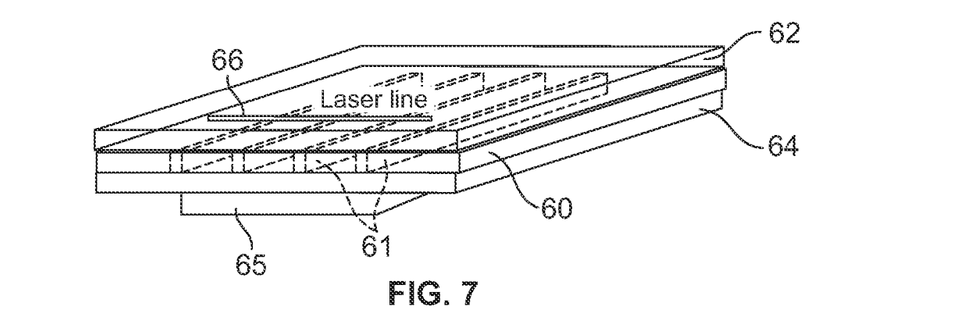
FIG. 7 is a schematic illustration of multiple sample streams according to another embodiment of the present disclosure.

FIG. 7 is a schematic illustration of yet another specific embodiment in which channels 61 are etched all the way through a silicon layer 60. In this embodiment the channels include both a glass top 62 and a glass bottom 64. As shown, an optional acoustic transducer 65 may be placed below the etched glass. This embodiment is also suitable for use in a system such as that shown in FIG. 1, wherein a laser line 66, is directed onto the array.

Figure 8:
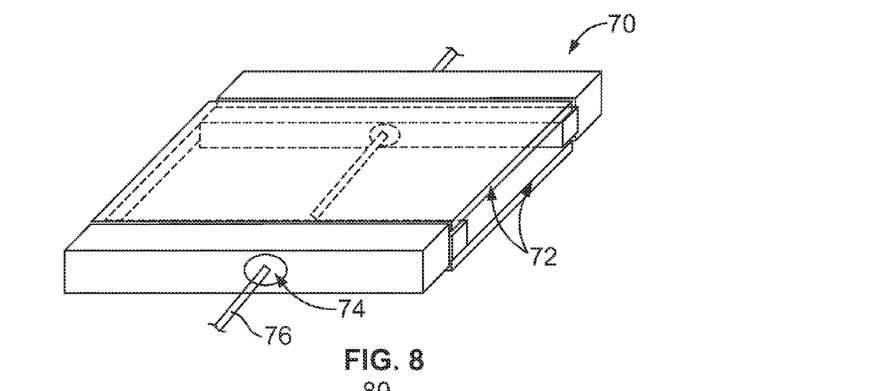
FIG. 8 is a schematic illustration of multiple sample streams according to a further embodiment of the present disclosure.

FIG. 8 is a schematic illustration of still another specific embodiment. In this embodiment a machined flow cell 70 includes glass sides 72 at the top and bottom which enable epiflourescence excitation and detection suitable for use for the system such as that shown in FIG. 1. Alternatively, or additionally, machined flow cell 70 may further include a laser window 74, which enables the use of this channel when a Bessel beam 76 (as shown in the embodiment depicted in FIG. 2) is used as the means of particle excitation.

It will be appreciated that when acoustic focusing is used to produce multiple flow streams in a single channel, it may be desirable to modify the channels so as to accommodate, enhance, or enable the acoustic focusing. For example, the channel sidewalls may further include wide PZT mounting regions that taper to the channel width to focus the acoustic energy into the aqueous media. Alternatively or additionally it will typically be desirable to control the vertical positioning of the particles, which ensures consistent particle velocity and minimizes the size of the optical interrogation volume. This can be done, for example, by frequency matching to the height of the channel, using two transducers (FIG. 9), or through the use of shallow channels, where the channel height is only 2-5 times that of the particle diameter (FIG. 10).

Figure 9:
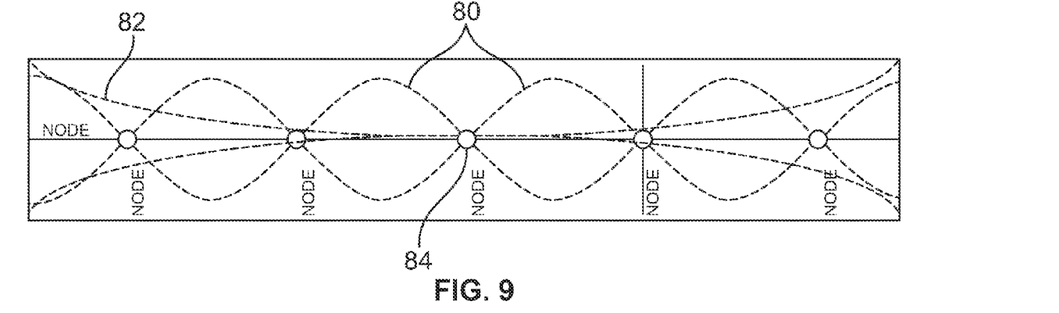
FIG. 9 is an end-on view of a channel employing either matched acoustic waves or two transducers in order to achieve vertical particle positioning.

FIG. 9 is an end-on view of a channel employing either matched acoustic waves or two transducers in order to achieve vertical particle positioning. In this depiction, the flow of the channel is out of the page. In this embodiment, matched acoustic waves 80 form a series of vertically constrained nodes. Alternatively, two transducers can be used to create a single vertical node 84. These methods of vertical constraint may be particularly desirable when deep channels are used.

Figure 10:
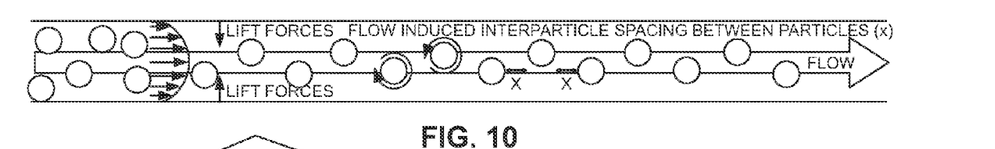
FIG. 10 is a schematic illustration showing the use of shallow channels as a means of vertical particle position control.

Alternatively or additionally, as shown in FIG. 10, shallow channels may be used as a means of both vertical position control, as particles are constrained top to bottom by the ceiling and floor of the channel. As the acoustic standing waves constrain the particles side-to-side, the inertial lift forces induced by the flow profile in the vertical direction are expected to drive even particle spacing and flow induced particle spacing at high particle concentrations. This spacing increases the maximum analysis rate by eliminating particle coincidences in the analysis area. These "inertial effects," which are effective when particles make up a significant fraction of the cross-section of flow channels, have been demonstrated in narrow inertial channels, but high particle concentrations in narrow channels also result in clogging issues. However, in the presently disclosed embodiment, because there is no physical barrier in the side-to-side direction, clogging issues are eliminated, which also enables faster flow and larger particle sizes.

Accordingly, while the system of the present disclosure is able to analyze particles that are less than 70 μm in diameter (the typical maximum diameter for particles analyzed with traditional flow cytometry systems), the system of the present disclosure is also able to easily analyze particles having a diameter of up to 1000 μm, including particles having diameters between 1 and 1000 μm, 70 and 1000 μm, 70 and 500 μm, 70 and 200 μm, and any other range in between. Furthermore, while the presently described system can accommodate flow rates of less than 250 μL/min (as are found in traditional flow cytometry systems), the present system can accommodate flow rates of up to 50 mL/min including flow rates of between 0 and 50 mL/min, 250 μL/min and 25 mL/min, 1 ml and 10 mL/min and any other range in between. Moreover, while the conventional flow cytometers analysis rates of 70,000 particles/second or less (as are found in traditional flow cytometry systems analyzing small particles), the present system can accommodate rates of up to $1\times10^6$ particles/second, including rates between 1 particle/second and $1\times10^6$ particles/s, $1\times10^4$ and $1\times10^6$ particles/s, $1\times10^5$ and $1\times10^6$ particles/s and any other range in between.

It will be appreciated that various combination of any or all of the above-described channel designs may be used to produce channels that are appropriate for specific areas of interest. For example, according to a specific exemplary embodiment, a high throughput flow cell might have 8-etched channels that are 148 μm in width by 40 μm in depth. When driven at 10 MHz each channel will support two acoustically focused flow streams. Using 46 μm walls between the channels will result in 8 channels providing 16 total flow streams over a 1.6 mm total width. The MHz drive frequency will be highly effective for focusing, as the radiation force of the acoustic standing wave is proportional to the drive frequency. Furthermore, >1 MHz acoustic standing waves do not lead to cavitation or cell damage. Additionally, the 40 μm channel depth will allow for vertical positioning and inertial spacing of cells, to increase analysis precision and rates. Channel number and dimension can vary for applications requiring high volumetric throughput but lower analysis rates or for large particle applications. In these cases, it may be desirable to use multiple large channels. For example, three 500×500 μm square channels that are spaced by 50 μm and driven at 1.48 MHz will generate a single node centered both vertically and horizontally in each channel.

According to an alternate specific exemplary embodiment, a flow cell might be designed to include 40 μm deep channels that are 1.6 mm wide and driven at 7.4 MHz, which will result in 16 streams across a 1.6 mm channel. Notably, these channels will be effectively usable at high linear velocities (~10 m/s) as the shallow 40 μm height will limit turbulent flow.

As a still further specific exemplary embodiment, for large particle applications, a flow cell could be designed to include channels that are 2000 μm wide and 400 μm deep. When driven at 1.48 MHz these channels will generate four flow streams, where the first and fourth stream are 250 μm from their nearest sidewalls and each stream is spaced from each other stream by 500 μm. Such a system could use particles up to roughly 350 μm in diameter and would be effective for large particle and high volume applications.

As stated above, once excitation of the particles in the flow stream array is achieved, the light resulting from this excitation is collected and imaged onto one or more array detectors. According to various embodiments optical collection is performed by means of an epifluorescent collection path. Returning to FIG. 3, telescopes 26 may be used as beam expanders to enable placement of the optimal image size onto the array detector. Furthermore, masks 90 may be placed in the image plane of the array detectors to limit scatter from the flow cells and cross-talk between adjoining streams. Masks with 20 μm resolution may be constructed, for example, from 500 μm thick silicon wafers using deep reactive ion etching. Alternatively, slits 92, may be made in the focal plane of each detector. Still viewing FIG. 3, it can be seen that the sample stream array and/or optical objective can be angled to accommodate various types of collection paths including epifluorescence, SSC (side scatter), and orthogonal fluorescence.

Viewing FIGS. 1, 2, and 3 as stated above, it can be seen that regardless of the particular configuration of the various component parts, in the disclosed system light from the excited particles is collected and directed towards one or more array detectors with a correlation of one detector per flow stream. Those of skill in the art will be familiar with a wide variety of array detectors that are suitable for use with the herein described system.

According to a first exemplary embodiment, an array detector comprising multiple PMTs may be used. One exemplary detector is the Hamamatsu H7260-20 PMT module (Hamamatsu Phototronics K.K., Hamamatsu City, JP) which has 32 channels, 200 μm spaces between 800 μm wide by 7 mm high sensors, a 200-020 nm spectral range, ns rise times, and a $10^6$ fold gain. These properties essentially provide 32 closely spaced PMTs with the performance characteristics that have made the PMT the dominant detector in flow cytometry. The presently described system images the flow stream onto these PMTs such that each flow stream can be correlated to an individual channel of the PMT.

Figure 11:
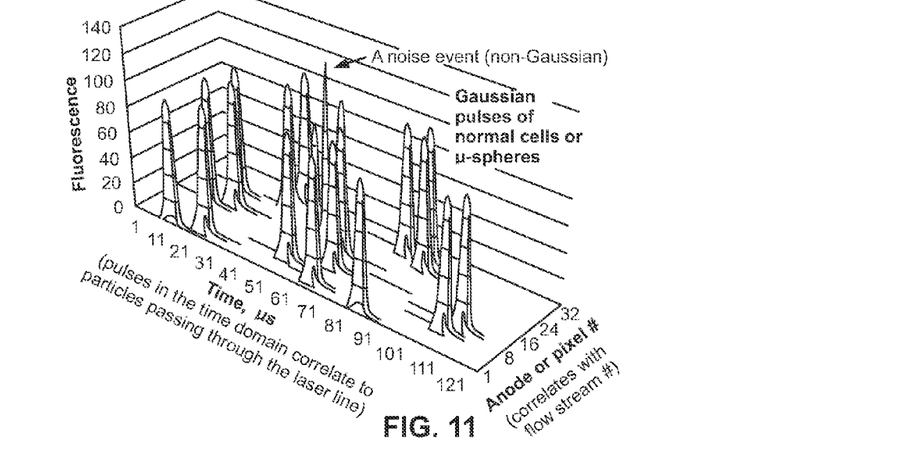
FIG. 11 is an illustration of how data might be presented in an exemplary embodiment of the present disclosure.

According to another embodiment, the array detector may be or incorporate an emCCD, CCD, or CMOS camera. In this case stream locations may be correlated to specific pixel locations in the cameras. An example emCCD is the Luca S (Andor Technology, PLC Belfast, Northern Ireland), which has a frame rate of 217 frames per second at 256 by 256 resolution. This offers two advantages: first, the higher resolution will enable the measurement of up to 100 flow streams; and second, the camera obviates the need for an acquisition system by directly streaming images that can be processed offline to quantify optical events. FIG. 11 provides a demonstration of the type of data that would be produced by such a system. Of course, emCCD, CCD, or CMOS cameras with increased sampling rates (>32,000 frames/second) could be used to increase analytical rates.

An exemplary experiment that could be performed using the system described herein is the detection of rare events in blood by simply diluting the blood sample and flowing the diluted sample through the system. In order to detect rare events in blood, like, for example, circulating tumor cells, the system should be able to detect 100 target cells per $cm^3$ of blood that contains $5\times10^9$ cells. To make this application work it will be critical to match volumetric delivery rates with analytical rates. To do this we will dilute the blood 1000 fold to 1000 $cm^3$. Given a channel cross-section of 1600 μm by 40 μm and a linear velocity of 5 m/s at the peak of the parabolic flow profile (a mean linear velocity of ~2.5 m/s), our volumetric delivery rate will be ~10 $cm^3$/in. This yields a volumetric analysis time of ~100 minutes. To compare analytical to volumetric delivery rates, consider that we will have to analyze all of the cells in the sample and assume a ~45% hematocrit value for normal blood ($5\times10^9$ cells would originally be contained in 0.45 cm3). This allows us to estimate that each cell will be $9\times10^{11}$ $cm^3$, which allows the diameter of spherical cell to be calculated as ~6 μm. The concentration factor of our proposed acoustic flow cell, which is calculated by the ratio of the cross-sectional area of our flow cell to that of the focused streams (~6 μm by 6 μm×16 streams), is 111. This will concentrate blood cells in the focused streams back to a fraction of that of normal blood, (~45% cells by volume*111/1000=5% cell to volume ratio). Therefore, given an even cell distribution, each cell would be separated by an equivalent volume of 20 cells ($1.8\times10^9$ $cm^3$). Assuming a cylindrical focused stream equivalent in diameter to a single cell allows the distance between cells to be calculated from the volume formula of the cylinder [distance=volume/$\pi*r2=1.8\times10^{-9}$ $cm^3/(\pi*(3\times10^{-6})^2)$ $cm^2$] or 64 pm. Our model assumes 5 m/s cell velocity in the focused stream, a 6 μm diameter cell, and 64 μm center to center gaps (edge to edge gaps of 58 μm). Therefore, when using a 20 μm wide laser beam the traversal time of a 6 μm diameter cell (from front edge entering the beam to trailing edge exiting) will be ~5 μs. Similarly, the gap between the trailing edge of one particle exiting the beam, and the leading edge of a successive particle entering the beam will be ~8 μs. This is an acquisition rate of 1 cell every 13 μs or ~77,000 cell/s per stream, which is ~$1.23\times10^6$ cells/s for 16-streams. At this rate it would take ~70 minutes to analyze $5\times10^9$ cells, achieving the desired optimal performance of approximately equal analytical and volumetric rates. These models demonstrate that our platform can detect as few as 100 cells/mL of blood using only dilution followed by analysis. This task would take days using a conventional flow cytometer. Instruments with 32 to 100 streams will enable either more forgiving flow rates or even higher analysis rates.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. A system for detecting flowing particles in multiple flow streams, the system comprising:
    a sample stream array comprising multiple flow streams generated by an acoustic transducer;
    a light beam configured to interrogate the multiple flow streams and provide spatially continuous excitation across the multiple flow streams including intervening spaces between streams;
    an optical objective configured to collect light emitted from excited particles flowing within the sample streams and image the light onto an array detector, wherein light emitted from each flow stream is individually identified and distinguished from light emitted from any other flow stream by its location on the array detector.

2. The system of claim 1 further comprising at least one channel wherein at least two streams in the sample stream array are contained within a single channel.

3. The system of claim 2 wherein the acoustic transducer is within sufficient proximity to the channel to produce an acoustic wave within the channel.

4. The system of claim 2 wherein the channel is formed in a substrate.

5. The system of claim 4 wherein the acoustic transducer is connected to the substrate.

6. The system of claim 5 comprising a second acoustic transducer connected to the substrate.

7. The system of claim 4 wherein the substrate contains a window positioned such that a light beam directed through the window will cross all of the sample streams in the sample stream array.

8. The system of claim 7 wherein the light beam is a Bessel beam.

9. The system of claim 4 wherein at least a portion of the substrate is formed from an optically clear material.

10. The system of claim 2 wherein the system comprises multiple channels.

11. The system of claim 1 wherein the detector is an array of PMTs and each flow stream is correlated to an individual PMT.

12. The system of claim 1 wherein the detector is a digital camera and each flow stream is correlated to a pixel location in the camera.

13. The system of claim 1 further comprising one or more telescopes configured to adjust the size of a light path.

14. The system of claim 1 wherein the detector further comprises a mask.

15. The system of claim 1 wherein the system collects background information from the intervening spaces.

16. The system of claim 1 wherein the system interrogates particles within the flow profile of the multiple flow streams.

17. A method for detecting particles flowing in multiple sample streams, the method comprising:
    flowing a sample containing particles through multiple sample streams generated by an acoustic transducer;
    directing light across the multiple sample streams such that the light provides spatially continuous excitation across all of the sample streams including in the intervening spaces between the streams;
    collecting light emitted from the sample streams by the excitation of the particles flowing in the sample streams and directing the emitted light towards a detector light emitted from each flow stream is individually identified and distinguished from light emitted from any other flow stream.

18. The method of claim 17 wherein the multiple sample streams flow through a channel, the method further comprising directing an acoustic wave field through the channel so as to constrain the pathway of the particles in the sample.

19. The method of claim 18 wherein the sample is suspected of containing a target of interest; the method further comprising exposing the sample to a plurality of negative acoustic contrast particles having functionally stable biomolecules attached thereto under sufficient conditions that the biomolecules are able to capture the target wherein the acoustic wave field focuses the negative acoustic contrast particles to their pressure potential maxima.

20. The method of claim 19 wherein the acoustic standing waves produce multiple nodes, and each node results in a discrete sample stream.

21. The method of claim 17 further comprising collecting light emitted from the intervening spaces between the streams.

22. The method of claim 17 wherein the excited particles are flowing in the flow profile of the flow stream.

23. A system for detecting particles in multiple flow streams, the system comprising:
    at least one channel containing multiple flow streams generated by an acoustic transducer;
    a light beam configured to interrogate the multiple flow streams and provide spatially continuous excitation across all of the streams including in the intervening spaces between the streams;
    an optical objective configured to collect light from excited particles flowing in the sample streams and image the light onto an array detector, wherein light emitted from each flow stream is individually identified and distinguished from light emitted from any other flow stream by its location on the array detector.

24. The system of claim 23 further comprising multiple channels, wherein each channel contains two or more flow streams.

25. The method of claim 23 wherein the system collects background information from the intervening spaces.

* * * * *